United States Patent [19]

Mirajkar et al.

[11] Patent Number: 5,800,803
[45] Date of Patent: Sep. 1, 1998

[54] ORAL COMPOSITION EXHIBITING ENHANCED UPTAKE BY DENTAL TISSUE OF NONCATIONIC ANTIBACTERIAL AGENTS

[75] Inventors: Yelloji Rao K. Mirajkar, Piscataway; Abdul Gaffar, Princeton, both of N.J.; Stefan Stein, Saulheim, Germany; Ekkehard Jahns, Weinheim, Germany; Reinhold Dieing, Bad Dürheim, Germany; Karin Sperling, Neustadt, Germany

[73] Assignee: Colgate-Palmolive Company, New York, N.Y.

[21] Appl. No.: 799,639

[22] Filed: Feb. 10, 1997

[51] Int. Cl.⁶ .............................. A61K 7/16; A61K 7/22; A61K 31/785; A61K 31/79
[52] U.S. Cl. ............................................. 424/54; 424/49
[58] Field of Search ............................................. 424/49–58

[56] References Cited

U.S. PATENT DOCUMENTS

| | | |
|---|---|---|
| 3,629,477 | 12/1971 | Model. |
| 3,980,767 | 9/1976 | Chown. |
| 3,996,863 | 12/1976 | Osborn. |
| 4,022,880 | 5/1977 | Vinson. |
| 4,139,485 | 2/1979 | Imokawa. |
| 4,152,421 | 5/1979 | Tsutsumi. |
| 4,328,205 | 5/1982 | Taylor. |
| 4,350,680 | 9/1982 | Harvey. |
| 4,358,437 | 11/1982 | Duke. |
| 4,435,380 | 3/1984 | Pader. |
| 4,871,396 | 10/1989 | Tsujita. |
| 4,894,220 | 1/1990 | Nabi. |
| 4,980,153 | 12/1990 | Jackson. |
| 5,015,471 | 5/1991 | Birtwistle. |
| 5,019,373 | 5/1991 | Carter. |
| 5,032,386 | 7/1991 | Gaffar. |
| 5,043,154 | 8/1991 | Gaffar. |
| 5,112,613 | 5/1992 | Honda. |
| 5,139,781 | 8/1992 | Birtwistle. |
| 5,156,601 | 10/1992 | Lorenz et al. ........................ 604/307 |
| 5,180,579 | 1/1993 | Birtwistle. |
| 5,258,421 | 11/1993 | Lorenz et al. ........................ 523/111 |
| 5,292,526 | 3/1994 | Gaffar et al. ........................ 424/52 |
| 5,334,375 | 8/1994 | Nabi et al. ........................ 424/52 |
| 5,368,844 | 11/1994 | Gaffar. |
| 5,370,865 | 12/1994 | Yamagishi. |
| 5,374,418 | 12/1994 | Oshino. |
| 5,420,197 | 5/1995 | Lorenz et al. ........................ 525/54.3 |
| 5,466,437 | 11/1995 | Gaffar et al. ........................ 424/52 |
| 5,538,715 | 7/1996 | Gaffar et al. ........................ 424/52 |
| 5,605,676 | 2/1997 | Gaffar. |
| 5,614,310 | 3/1997 | Delgado et al. ........................ 428/316.6 |
| 5,670,138 | 9/1997 | Venema et al. ........................ 424/52 |

FOREIGN PATENT DOCUMENTS

| | | |
|---|---|---|
| 0 691 124 A1 | 1/1996 | European Pat. Off.. |
| 6271440 | 9/1994 | Japan. |

OTHER PUBLICATIONS

Harry's Cosmeticology, Seventh Edition, Chemical Publishing, New York, pp. 609–616, 1982.

J. Clinical Periodontal 1992; 19: 322–335, Rundegren et al, "Effect of 4 days of mouth rinsing with delmopinol or chlorhexidine on the vitality of plaque bacteria".

International Dental Journal, 1994, vol. 44, No. (Supplemental), Gaffar et al, "Recent advances in plaque, gingivitis, tartar and caries prevention technology".

American Journal of Dentistry, 1990; 3: S7–S14; Gaffar et al; "Antiplaque effects of dentifrices containing triclosan/copolymer/NaF system versus triclosan dentifrices without the copolymer".

Primary Examiner—Shep K. Rose
Attorney, Agent, or Firm—Henry S. Goldfine

[57] ABSTRACT

An oral composition and method for use thereof, comprising in an orally acceptable vehicle, an effective antiplaque amount of a noncationic antibacterial agent, and an anionic copolymer formed from monomers of which about 40 to about 90% by weight are hydrophilic type capable of attachment to oral surfaces and about 10 to about 60% by weight are of a hydrophobic type; such oral composition being effective in increasing the uptake of the antibacterial compound to dental tissue so as to enhance the therapeutic efficacy of the administered antibacterial compound.

14 Claims, No Drawings

ORAL COMPOSITION EXHIBITING ENHANCED UPTAKE BY DENTAL TISSUE OF NONCATIONIC ANTIBACTERIAL AGENTS

BACKGROUND OF THE INVENTION

1. Field of the Invention

The present invention relates to oral care compositions exhibiting improved uptake on dental tissue of noncationic antibacterial compounds.

2. The Prior Art

Intraoral surfaces, either soft or hard, frequently are covered by a bacterial deposit called "plaque". Such dental plaque is a soft deposit which adheres tenaciously at the points of irregularity or discontinuity on dental tissue, e.g., on rough calculus surfaces, at the gum line and the like. Plaque generally consists of about 70% by weight bacteria, with the balance comprised of host cells, food debris, proteins, polysaccharides, etc. Besides being unsightly, plaque is implicated in the aetiology of caries and periodontitis, which together are responsible for about 95% of tooth loss.

As disclosed in U.S. Pat. No. 5,043,154 a wide variety of noncationic antibacterial agents have been suggested in the art to retard plaque formation and the oral infections and dental disease associated with plaque formations. For example, halogenated hydroxydiphenyl ether compounds such as Triclosan are well known to the art for their antibacterial activity and have been used in oral compositions to counter plaque formation by bacterial accumulation in the oral cavity.

Although antibacterial agents such as Triclosan are highly effective in killing bacteria which are responsible for plaque formation, it is difficult to maintain an effective level of such agents on dental tissue for a significant time period after their application. As disclosed in U.S. Pat. No. 4,894,220, or U.S. Pat. No. 5,032,386 certain polymeric polycarboxylates, such as vinyl ether-maleic anhydride copolymers, enhance the delivery and retention of the antibacterial agent on dental tissue. EP-A 691,124 discloses the use of copolymers of acrylic acid and N-vinylpyrrolidone for improving the bioadhesion of bactericidal compounds.

Due to the above mentioned polymeric materials, once applied, the antibacterial compound is maintained in a continuing adherence to the teeth and adjacent oral gingival mucosa, thereby retarding washout of the antibacterial compound from infected areas of dental tissue by saliva present in the mouth Accordingly, the greater the contact time facilitated between the antibacterial agent and the dental tissue the more efficacious the antibacterial effect. There is therefore a continuous interest in the art to provide means whereby nonionic antibacterial compounds contained in oral care compositions can be more efficaciously delivered to and retained on dental tissue for extended periods of time.

SUMMARY OF THE INVENTION

In accordance with this invention there is provided an oral composition comprising an orally acceptable aqueous vehicle, an effective antiplaque amount of a noncationic antibacterial agent, and an amount of an anionic copolymer formed from a balanced ratio of monomers, wherein at least about 40 to about 90% by weight of the copolymer is derived from a hydrophilic type monomer, including acrylamidomethylpropylsulfonic acid, an alpha,beta-ethylenically unsaturated carboxylic, sulfonic, phosphonic or phosphate acid or its salts, capable of attachment to the oral surfaces and at least about 10 to about 60% by weight of the copolymer is derived from a hydrophobic type monomer. The presence in the oral composition of the copolymer enhances the uptake of the antibacterial agent to and retention on oral surfaces, whereby the antibacterial therapeutic efficacy of the administered composition is enhanced.

The enhanced uptake of the noncationic antibacterial agent on dental tissue observed with the practice of the present invention is unexpected. The reason for such an enhancement is not known and the present invention is not to be restricted to any theory. However, for whatever help it may provide in understanding the invention, it is suggested that the observed enhanced uptake of the noncationic antibacterial agent is due to the dual presence of hydrophilic and hydrophobic groups in the anionic polymer, the hydrophilic groups enhancing attachment to the dental tissue and the hydrophobic groups promoting solubilization of the substantially water insoluble noncationic antibacterial agent in the aqueous vehicle of the oral composition.

DETAILED DESCRIPTION OF THE PREFERRED EMBODIMENTS

The term "oral composition" is used herein to designate dental products which, in the ordinary course of usage, are retained in the oral cavity for a time sufficient to contact substantially all of the dental surfaces, but are not intentionally ingested. Such products include, but are not limited to, dentifrices, gels, mouthwashes, chewing gums and lozenges.

In the preparation of an oral composition, in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 30% to about 60% by weight and the humectant concentration typically totals about 40 to about 60% by weight of the oral composition.

In the practice of the present invention, the noncationic antibacterial agent is present in the oral composition in an effective antiplaque amount, typically about 0.01 to about 2% by weight, preferably about 0.1 to about 1% by weight. Noncationic antibacterial agents useful in the practice of the present invention are phenolic compounds of the type disclosed in U.S. Pat. No. 5,368,844, which disclosure is herein incorporated by reference. Typical phenolic compounds include phenol and its homologs, such as 2,4-dimethylphenol, 4-n-butyl phenol, 4-n-amyl phenol and 4-n-heptyl phenol, 2-methoxy-4-(2 propenyl)-phenol and 2-isopropyl-5-methyl phenol; mono and polyalky and aromatic halophenols, such as 4-chloro-2-methyl phenol, 5-chloro-2-hydroxydiphenylmethane, 2-phenyl phenol, n-hexyl 0-bromophenol, and 6-iso-propyl-2-ethyl-3-methyl p-chlorophenol; resorcinol and its derivatives, such as, n-butyl resorcinol, n-nomyl resorcinol, phenylpropyl resorcinol, and 2,4-dihydroxydiphenyl methane; and bisphenolic compounds, such as 2,2'-methylene bis (4-chlorophenol), and bis (2-hydroxy-3,5-dichlorophenyl) sulfide. A preferred phenolic antibacterial agent is a halogenated diphenyl ether, such as Triclosan.

Hydrophilic monomers used to prepare the anionic copolymers of the present invention, having the requisite hydrophilicity, are well known to the art and include alpha, beta-ethylenically unsaturated carboxylic, sulfonic, phosphonic acids, such as acrylic acid or methacrylic acid and their alkali metal salts such as sodium acrylate, sodium methacrylate, potassium acrylate and potassium methacrylate. Other useful alpha,beta-ethylenically unsaturated carboxylic acid hydrophilic monomers include crotonic, fumaric, maleic, itaconic, and methylen malonic acids.

Alpha,beta-ethylenically unsaturated sulfonic acids include vinylsulfonic acid and acrylamidomethylpropylsulfonic acid (hereinafter referred to as "AMPS") and their alkali metal and ammonium salts. Vinyl phosphonic acid is an example of a useful alpha,beta-ethylenically unsaturated monomer having a phosphonic or phosphate residue.

Hydrophobic type monomers used to prepare the copolymers of the present invention include an alkyl-group that contains 1–30 carbon atoms, preferably 1 to 8 carbon atoms, such as methylacrylate, methy or ethyl methacrylate, n-propyl acrylate or -methacrylate, i-propyl acrylate or -methacrylate and n-butyl, i-butyl, t-butyl acrylate or -methacrylate, hydroxyalkyl (meth)acrylate with alkyl being $C_1$–$C_4$, and polyethylenglycol (meth)acrylates. Other hydrophobic monomers include styrene, substituted styrene and N-vinylcaprolactam, N-vinylpiperidone, N-vinylpyrrolidone, N-methyl-N-vinylacetamide, N-vinylformamide, vinylacetate, vinylpropionate and substituted acrylamides such as tert.butylacrylamide and octylacrylamides.

The anionic copolymer used in the practice of the present invention generally is derived from about 40 to about 90% by weight of a hydrophilic type monomer and preferably about 50 to about 80% by weight of the hydrophilic monomer and about 10 to about 60% by weight of the hydrophobic type monomer and preferably 20 to about 50% by weight of the hydrophobic monomer.

Hydrophilic monomers preferred for use in the formation of anionic copolymers in accordance with the practice of the present invention include acrylic acid and AMPS and their sodium salts. Hydrophobic monomers preferred for use in the preparation of the copolymers of the present invention include styrene and methyl(meth)acrylate and ethylacrylate.

A preferred anionic copolymer comprised of both hydrophilic and hydrophobic monomers has the general formula: ABC, wherein; A is styrene, B is methylacrylate and C is selected from a mixture of acrylic acid and AMPS. This preferred anionic copolymer is formed containing about 0.5 to about 50% by weight A, preferably about 5% by weight A, 0 to 50% by weight B, preferably about 0.05 to about 25% by weight B, and about 40 to about 90% by weight C, preferably about 80% by weight C.

A second preferred anionic copolymer for use in the practice of the present invention is one having the general formula: XY, wherein; X is N-vinylcaprolactam and Y is selected from acrylic acid, methacrylic acid or the sodium salt thereof. X is present in the copolymer at a concentration of about 10 to about 60% by weight, preferably about 30 to about 60% by weight, and Y is present in the copolymer at a concentration of about 40 to about 90% by weight, and preferably about 40 to about 70% by weight.

It is preferred that the anionic copolymer used in the practice of the present invention have an average molecular weight (MW) of at least 10,000 to about 5,000,000 and preferably about 20,000 to about 2,000,000 to avoid possible human systemic toxicity, that is assimilation in the body.

The molecular weight of the polymer can be regulated by using mercaptoalkyl carboxylic acid or alcohol chain transfer agents, such as thioglycolic acid, 3-mercaptopropionic acid and 2-mercaptoethanol, as well as mixtures thereof.

The anionic copolymer of the present invention having both hydrophilic and hydrophobic groups is incorporated in the oral composition of the present invention in an amount effective to enhance the uptake of the noncationic antibacterial agent, typically, about 0.5 to about 5% by weight, preferably about 1 to 3% by weight, and most preferably about 1.5 to about 2.5% by weight.

A representative and especially preferred anionic copolymer is the sodium salt of a methylacrylate/styrene/AMPS/acrylic acid copolymer (hereinafter AMPS terpolymer salt), containing as hydrophilic monomers about 45 to about 65% by weight of AMPS, about 15 to about 30% by weight acrylic acid, and as hydrophobic monomers about 5 to about 25% of methyl or ethyl acrylate and a styrenic monomer, such as styrene or methyl styrene at about 0.1 to about 2% by weight. The AMPS terpolymer salt is prepared by procedures well know to the art, wherein the monomers are copolymerized in the presence of a free radical polymerization initiator, such as peroxide, azo and redox systems.

In general, the polymerization reaction to prepare the AMPS terpolymer salt can be in bulk, solution, emulsion or suspension at a temperature between 10° C. and 100° C. The reaction rate is a function of temperature, and completion will occur generally from 2 minutes to 12 hours.

The AMPS terpolymer salt is typically prepared by mixing AMPS and acrylic acid in deionized water and neutralizing the resultant mixture with an alkaline agent, such as, sodium hydroxide (feed 1). Styrene is dissolved in methylacrylate (feed 2). Water is introduced into the vessel and heated to about 60° to about 90° C. Feed 1, feed 2 and the polymerization initiator are added within 2 to 3 hours. A clear solution or a milky dispersion of the AMPS terpolymer salt is obtained, depending on the ratio of hydrophilic to hydrophobic monomers.

A second anionic copolymer having both hydrophilic and hydrophobic groups preferred for use in the present invention is a copolymer of N-vinylcaprolactam and an alkali metal acrylate, such as sodium acrylate. The anionic copolymer is comprised of about 50% by weight of the vinyl caprolactam and about 50% by weight of the alkali metal acrylate.

The N-vinylcaprolactam/alkali metal acrylate copolymer salt (hereinafter VCAP copolymer salt) is prepared in an aqueous or aqueous-alcohol solution, by subjecting the vinyl caprolactam and alkali metal acrylate monomers, at a solids content of about 15 to 30%, to a temperature of about 75° C., under agitation in an inert atmosphere, for a period of about 8 hours, in the presence of about 0.1 to 5% by weight based upon total monomers of a free radical polymerization initiator or catalyst, such as hydrogen peroxide or an azo compound, such as azobisisobutyronitrile.

In the preparation of the oral compositions of the present invention useful anionic surfactants are included in the composition for production of foam and to aid in cleaning and removal of debris; these anionic surfactants include the higher fatty acid monoglyceride monosulfates, such as the sodium salts of the monosulfated monoglycerides of hydrogenated coconut oil fatty acid; higher alkyl sulfates, such as sodium lauryl sulfate; higher alkl aryl sulfonates, such as sodium linear dodecyl benzene sulfonate; higher olefin sulfonates, such as sodium higher olefin sulfonate in which the olefin group is 12 to 21 carbon atoms; higher alkyl alkali sulfoacetates such as sodium lauryl sulfoacetate; higher fatty acid esters of 1,2-dihydroxypropane sulfonates, the substantially saturated higher aliphatic acyl amides of lower aliphatic aminocarboxylic acid alkali metal salts, such as those having 12 to 16 carbon atoms in the fatty acyl radicals; higher alkyl poly-lower alkoxy sodium sulfates; higher fatty acid sodium and potassium soaps of coconut oil and tallow, and the like. The anionic surfactant, sodium lauryl sulfate, is preferred for use in the practice of the present invention.

The anionic surfactant is included in the oral composition of the present invention at a concentration of about 0.1 to about 5% by weight and preferably about 0.5 to about 3% by weight.

Oral compositions in the form of a dentifrice, such as toothpastes, also typically contain polishing materials including crystalline silica, having a particle size of up to about 20 microns, such as commercially available Zeodent 115, silica gel or colloidal silica, complex amorphous alkali metal aluminosilicates, hydrated alumina, calcined alumina, sodium metaphosphate, sodium bicarbonate, calcium carbonate, calcium pyrophosphate, dicalcium phosphate and dicalcium phosphate dehydrate. Typically, the polishing material is included in semi-solid or pasty dentifrice compositions of the present invention in an amount of from about 15 to about 60% by weight and preferably from about 20 to about 55%.

Pyrophosphate salts having antitartar efficacy such as a dialkali or tetraalkali metal phosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphate such as sodium trimetaphosphate may be incorporated in oral compositions of the present invention preferably at concentration of about 0.5 to about 8.0% by weight and preferably about 0.5 to about 3.0% by weight. In liquid oral preparations, the pyrophosphate salts are incorporated at a concentration of about 0.1 to about 2% by weight.

Dentifrices prepared in accordance with the present invention typically contain a natural or synthetic thickener in proportions of about 0.1 to about 5% by weight, preferably about 0.5 to about 2% by weight. Suitable thickeners include Irish moss, i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose and colloidal silica.

The oral composition may also contain a source of fluoride ions, or fluoride-providing compound, as an anticaries agent, in an amount sufficient to supply about 25 ppm to 5,000 ppm of fluoride ions and preferably 500 to 1500 ppm fluoride ions. Among these compounds are inorganic water soluble fluoride salts, such as the alkali metal salts, for example, sodium fluoride, potassium fluoride, sodium fluorosilicate, ammonium flourosilicate and sodium monofluorophosphate, as well as tin fluorides, such as stannous fluoride and stannous chloride.

Any suitable flavoring or sweetening material may also be employed in the preparation of the oral compositions of the present invention. Examples of suitable flavoring constituents include flavoring oils, e.g. oil of spearmint, peppermint, wintergreen, clove, sage, eucalyptus, marjoram, cinnamon, lemon, orange, and methyl salicylate. Suitable sweetening agents include sucrose, lactose, maltose, xylitol, sodium cyclamate, aspartyl phenyl alanine methyl ester, saccharine and the like. Suitably, flavor and sweetening agents may each or together comprise from about 0.1% to 5% more of the oral composition.

Various other materials may be incorporated in the oral preparations of this invention such as whitening agents, including urea peroxide, calcium and hydrogen peroxide, preservatives, vitamins such as vitamin B6, B12, C, E and K, silicones, chlorophyll compounds and potassium salts for the treatment of dental hypersensitivity such as potassium nitrate and potassium citrate. These agents, when present, are incorporated in the compositions of the present invention in amounts which do not substantially adversely affect the properties and characteristics desired.

The manufacture of the oral composition of the present invention is accomplished by any of the various standard techniques for producing such compositions. To make a dentifrice, a vehicle is prepared containing glycerol, sorbitol, propylene glycol, gelling agents, anionic copolymer and a noncationic antibacterial agent such as Triclosan. One or more surfactants are added to the vehicle, followed by blending in of a polishing agent, as sell as, any polyphosphate and fluoride salts. Finally, any flavoring agent is admixed and the pH of the composition is adjusted to between 6.8 to 7.0.

The following examples are further illustrative of the present invention, but it is understood that the invention is not limited thereto. All amounts and proportions referred to herein and in the appended claims are by weight, unless otherwise so stated.

EXAMPLE I

The effect on noncationic antibacterial agent uptake on dental tissue of anionic copolymers of the present invention containing both hydrophilic and hydrophobic groups was assessed using disks of hydroxyapatite (HAP) available from Clarkson Chromatography Products, Inc., which were saliva coated (SCHAP), as an in vitro model for human teeth. This in vitro model has been found to be corelatable to in vivo delivery of and retention of antibacterial agents on oral surfaces.

To determine the delivery and retention of Triclosan to a SCHAP disk from a dentifrice containing Triclosan and an anionic copolymer of the present invention, namely AMPS terpolymer, and VCAP copolymer, SCHAP disks were treated with dentifrice slurry compositions identified in Table I below as Compositions A, and B respectively. The amounts of dentifrice slurry used to contact the disks simulated in vivo surface to volume ratios found in the mouth. The dentifrice slurries were a liquid phase solution which contained all the components of a dentifrice except the abrasive. The liquid phase, in part, simulates brushing condition. After incubation for 30 minutes at 37° C., the SCHAP disks were removed from the dentifrice slurry and washed three times with water. The uptake absorption of Triclosan, on SCHAP disks, from Compositions A and B is set forth in Table II, below, ordered by weight ratio of hydrophilic to hydrophobic monomer in each copolymer.

For purposes of comparison, the procedure of Example I was repeated, except comparative copolymers of varying weight ratios of hydrophilic and hydrophobic monomers were substituted at the 2% by weight levels for the anionic copolymers used in Example I. These comparative polymers included:

100% acrylamidomethylpropylsulfonic acid, MW of about 500,000, designated Composition C;

75% vinylpyrrolidone/25% acrylamidomethylpropylsulfonic acid, MW of about 500,000, designated Composition D;

5% styrene/95% acrylic acid, MW of about 800,000, designated Composition E;

The uptake absorption of Triclosan, on SCHAP disks, from comparative compositions C-E is also set forth in Table II, below.

TABLE I

| Composition Ingredients | A Wt. % | B Wt. % |
| --- | --- | --- |
| Sorbitol | 20.0 | 20.0 |
| Glycerol | 20.0 | 2.0.0. |
| Propylene Glycol | 0.5 | 0.5 |
| Sodium Lauryl Sulphate | 1.5 | 1.5 |
| AMPS terpolymer salt polymer* | 2.0 | — |
| VCAP** | — | 2.0 |
| Triclosan | 0.3 | 0.3 |
| NaF | 0.243 | 0.243 |
| Water | 53.857 | 53.857 |
| Flavor Oil | 1.0 | 1.0 |
| NaCH | 0.6 | 0.6 |
| Total | 100.0 | 100.0 |

*20% methyl acrylate, 1% styrene, 59% AMPS, and 20% Acrylic Acid, MW = about 1,200,000.
**50% vinylcaprolactam, and 50% acrylic acid, MW = about 1,000,000.

TABLE II

| Weight Ratio of Hydrophilic to Hydrophobic Monomer In Copolymer | Composition | Uptake of Triclosan (µg/Disk) | Standard Deviation* |
| --- | --- | --- | --- |
| 79:21 | A | 120.96 | +/− 20.33 |
| 50:50 | B | 97.99 | +/− 16.27 |
| 100:0 | C | 52.74 | +/− 3.98 |
| 25:75 | D | 47.22 | +/− 2.77 |
| 95:5 | E | 3.25 | +/− 0.28 |

*Standard deviation ± from µg of Uptake shown.

The results presented in Table II show that the delivery and retention of Triclosan to SCHAP disks from the Comparative compositions C, D, E and F were substantially less than from Compositions A and B which exhibited Triclosan uptakes of 120.96 and 97.99, respectively

EXAMPLE II

The efficacy of Compositions A and B, of the subject invention, were compared to a standard of water alone, Composition F, to determine their ability to inhibit bacterial plaque formation in vitro using the chemostat plaque model as described in Gaffar et al, Am. J. Dent., Vol. 3, Special Issue pages 58–59, (September 1990). The experimental apparatus includes a chemostat (Bioflo, Model C32), a source of supplementing growth media, a mixing chamber and several flow cells- The flow cells were specifically designed to contain 13mm×1 mm thick SCHAP disks on which plaque formation was measured.

A mixed culture of five species of oral microorganisms (A. viscosus, S. mutans, S. sanguis, V. parvula, and F. nucleatum) associated with human plaque was maintained in the chemostat, and the culture was then pumped through the flow cells at the rate of 1 ml/minute for 48 hours to grow plaque on the disks. Thereafter the liquid dentifrices were pumped for 30 seconds at the rate of 1 ml/minute through the flow cells containing SCHAP disks on which the plaque was grown. A total of four treatments of the SCHAP disks were given at 12 hour intervals during a 48 hour plaque growth period. Thereafter, bacterial plaque grown on the SCHAP disks was removed by immersion of the disks in a 2 ml solution of 0.1 N NaOH in a water bath at 37° C. with gentle shaking for 15 minutes. The disks were removed and the NaOH solution was sonicated to disperse the plaque. Turbidity (optical density, O.D.) of the sample was then determined by measuring the absorbance at 610 nm in a spectrophotometer which is turbidity reported as plaque score in Table III, below. Plaque scores indicate the degree of plaque growth on the SCHAP disks, that is the lower the plaque score, the greater the antiplaque activity of the dentifrice slurry being tested. The plaque scores of Compositions A, B and F are recorded in Table III, below.

TABLE III

| Composition | Plaque Score |
| --- | --- |
| A | 0.233 |
| B | 0.2063 |
| F | 0.34 |

The plaque scores recorded in Table III indicate that Compositions A and B, containing anionic copolymers of the present invention, were substantially more effective against plaque than the water standard, Composition F.

What is claimed is:

1. An oral composition exhibiting increased uptake by dental tissue of antibacterial compounds contained therein, the oral composition comprising an orally acceptable aqueous vehicle, an effective therapeutic amount of a noncationic antibacterial agent, and an anionic copolymer comprised of about 50% to about 80% by weight of a hydrophilic monomer capable of attachment to oral surfaces and about 20% to about 50% by weight of a hydrophobic monomer; the anionic copolymer containing the hydrophilic monomer acrylamidomethylpropylsulfonic acid or salts thereof, or the anionic copolymer containing the hydrophobic monomer N-vinylcaprolactam, or mixtures thereof.

2. The oral composition of claim 1, wherein the anionic copolymer is of the general formula ABC, wherein A is styrene, B is methylacrylate and C is a mixture of acrylic acid and the acrylamidomethylpropylsulfonic acid.

3. The oral composition of claim 2, wherein A is present in the copolymer at a concentration of about 0.5 to about 50% by weight, B is present in the copolymer at a concentration of 0 to about 50% by weight, and C is present in the copolymer at a concentration of about 40 to about 90% by weight.

4. The oral composition of claim 1, wherein the anionic copolymer is of the general formula XY, X being the N-vinylcaprolactam and Y being selected from acrylic acid, methacrylic acid or sodium salts thereof.

5. The oral composition of claim 4, wherein X is about 10 to about 60% by weight and Y is about 50 to about 80% by weight.

6. The oral composition of claim 1, wherein the antibacterial agent is incorporated in the oral composition at a concentration of about 0.05 to about 2.0% by weight.

7. The oral composition of claim 1, wherein the antibacterial agent is triclosan.

8. A method for the treatment and prevention of bacterial plaque accumulation on teeth which comprises preparing and administering to the oral cavity an oral composition comprising an orally acceptable aqueous vehicle, an effective therapeutic amount of a noncationic antibacterial agent, and an anionic copolymer formed from different monomers of which about 50% to about 80% by weight are of the hydrophilic type capable of attachment to oral surfaces and about 20% to about 50% by weight are hydrophobic type monomers; the anionic copolymer containing the hydrophilic monomer acrylamidomethylpropylsulfonic acid or the salts thereof, or the anionic copolymer containing the hydrophobic monomer N-vinylcaprolactam, or mixtures thereof.

9. The method of claim 8, wherein the anionic copolymer is of the general formula ABC, A being styrene, B being methylacrylate and C being a mixture of acrylic acid and the acrylamidomethylpropylsulfonic acid.

10. The method of claim 9, wherein A is present in the copolymer at a concentration of about 0.5 to about 50% by weight, B is present in the copolymer at a concentration of 0 to about 50% by weight, and C is present in the copolymer at a concentration of about 40 to about 90% by weight.

11. The method of claim 8, wherein the anionic copolymer is of the general formula XY, X being the N-vinylcaprolactam and Y being selected from acrylic acid, methacrylic acid or sodium salts thereof.

12. The method of claim 11, wherein X is about 10 to about 60% by weight and Y is about 50 to about 80% by weight.

13. The method of claim 8, wherein the antibacterial agent is incorporated in the oral composition at a concentration of about 0.05 to about 2.0% by weight.

14. The method of claim 8, wherein the antibacterial agent is triclosan.

* * * * *